US012633376B2

(12) United States Patent
Bose et al.

(10) Patent No.: US 12,633,376 B2

(45) Date of Patent: ***May 19, 2026

(54) SYSTEM AND METHOD FOR RISK ASSESSMENT OF AUTISM SPECTRUM DISORDER

(71) Applicant: Tata Consultancy Services Limited, Mumbai (IN)

(72) Inventors: Chandrani Bose, Pune (IN); Sharmila Shekhar Mande, Pune (IN); Harrisham Kaur, Pune (IN); Nishal Kumar Pinna, Pune (IN)

(73) Assignee: Tata Consultancy Services Limited, Mumbai (IN)

( * ) Notice: Subject to any disclaimer, the term of this patent is extended or adjusted under 35 U.S.C. 154(b) by 1139 days.

This patent is subject to a terminal disclaimer.

(21) Appl. No.: 17/633,138

(22) PCT Filed: Aug. 5, 2020

(86) PCT No.: PCT/IB2020/057397

§ 371 (c)(1),
(2) Date: Feb. 4, 2022

(87) PCT Pub. No.: WO2021/024198

PCT Pub. Date: Feb. 11, 2021

(65) Prior Publication Data

US 2025/0356948 A1 Nov. 20, 2025

(30) Foreign Application Priority Data

Aug. 5, 2019 (IN) .............................. 201921031560

(51) Int. Cl.
| | |
|---|---|
| *G16B 30/00* | (2019.01) |
| *C12Q 1/6869* | (2018.01) |
| *C12Q 1/6888* | (2018.01) |
| *G16B 40/20* | (2019.01) |
| *G16H 20/10* | (2018.01) |
| *G16H 50/30* | (2018.01) |

(52) U.S. Cl.
CPC ........... *G16B 30/00* (2019.02); *C12Q 1/6869* (2013.01); *C12Q 1/6888* (2013.01); *G16B 40/20* (2019.02); *G16H 20/10* (2018.01); *G16H 50/30* (2018.01); *C12Q 2600/118* (2013.01)

(58) Field of Classification Search
CPC ...... G16B 30/00; G16B 40/20; C12Q 1/6869; C12Q 1/6888; C12Q 2600/118; G16H 20/10; G16H 50/30
See application file for complete search history.

(56) References Cited

U.S. PATENT DOCUMENTS

| | | |
|---|---|---|
| 9,443,205 B2 | 9/2016 | Wall |
| 2014/0179726 A1 | 6/2014 | Bajaj et al. |

FOREIGN PATENT DOCUMENTS

| | | |
|---|---|---|
| EP | 3135772 B1 | 10/2019 |
| WO | WO2017/044886 A1 | 3/2017 |
| WO | WO2018/175759 A1 | 9/2018 |

OTHER PUBLICATIONS

Dovrolis N. Computational profiling of the gut-brain axis: microflora dysbiosis insights to neurological disorders. Briefings in Bioinformatics 20(3): 825-841. (Year: 2019).*

Matson Johnny L. et al., "A review of methodological issues in the differential diagnosis of autism spectrum disorders in children", Research in Autism Spectrum Disorders, Date: Mar. 2007, vol. 1, Issue: 1, pp. 38-54, Publisher: Elsevier https://citeseerx.ist.psu.edu/viewdoc/downlaod?doi=10.1.1.464.818&rep=rep1&type=pdf.

Nasser, Ibrahim M. et al., "Artificial Neural Network for Diagnose Autism Spectrum Disorder" International Conference on Trends in Electronics and Informatics (ICOEI), Date: Feb. 2019, Publisher: IEEE, http://dstore.alazhar.edu.ps/xmlui/bitstream/handle/123456789/277/ArtificialNeuralNetworkfor DiagnoseAutismSpectrum.pdf?sequence=1&isAllowed=y.

Martin, Clair R. et al., "The Brain-Gut-Microbiome Axis", Cell Mol Gastroenterol Hepatol, Date: 2018, vol. 6(2), pp. 133-148, Publisher: NCBI, https://www.cmghjournal.org/action/showPdf?pii=S2352-345X%2818%2930060-2.

International Search Report and Written Opinion mailed Mar. 12, 2021, in International Application No. PCT/IB2020/057397; 7 pages.

* cited by examiner

*Primary Examiner* — Olivia M. Wise
*Assistant Examiner* — Robert J. Kallal
(74) *Attorney, Agent, or Firm* — Finnegan, Henderson, Farabow, Garrett & Dunner, LLP

(57) ABSTRACT

A system and method for risk assessment of an individual for autism spectrum disorder (ASD) has been provided. The system is using a non-invasive method for risk assessment of the individual, especially children, for ASD through prediction of metabolic potential of the bacteria residing in gastrointestinal tract of the individual. The system is configured to calculate a score, evaluated from the gut bacterial community's taxonomic abundance profile, which is indicative of its metabolic potential for production of a particular neuroactive compound. A set of metabolic pathways harboured by the bacterial community residing in gut has been utilized to develop an ASD diagnosis scheme that, when applied with the conventional screening tests, help in early diagnosis of the ASD. Further, the present disclosure also provides bacterial community based therapeutic approaches that can potentially minimize the side effects through maintaining the healthy cohort of bacteria in gut.

12 Claims, 3 Drawing Sheets

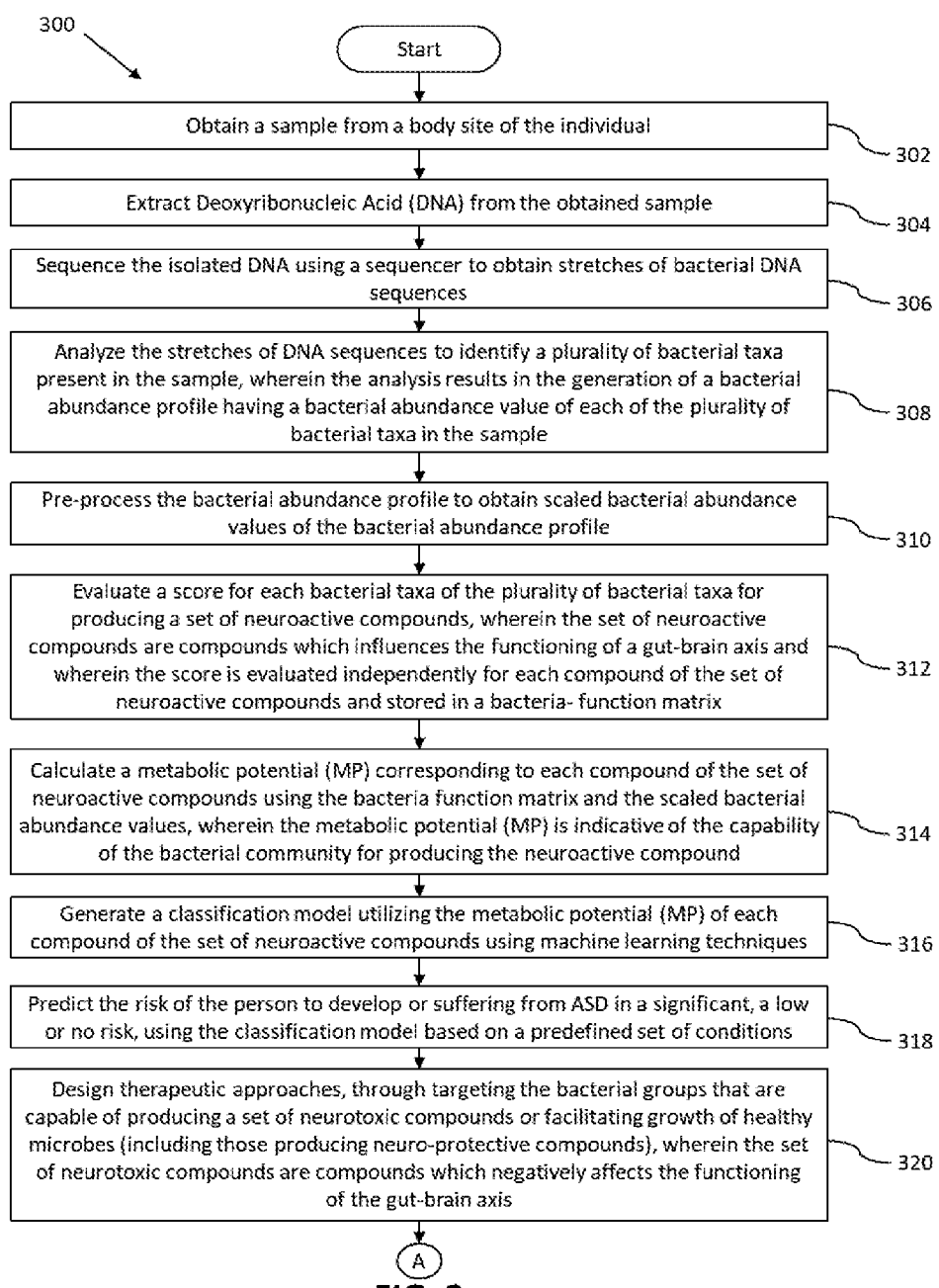

300

Start

Obtain a sample from a body site of the individual — 302

Extract Deoxyribonucleic Acid (DNA) from the obtained sample — 304

Sequence the isolated DNA using a sequencer to obtain stretches of bacterial DNA sequences — 306

Analyze the stretches of DNA sequences to identify a plurality of bacterial taxa present in the sample, wherein the analysis results in the generation of a bacterial abundance profile having a bacterial abundance value of each of the plurality of bacterial taxa in the sample — 308

Pre-process the bacterial abundance profile to obtain scaled bacterial abundance values of the bacterial abundance profile — 310

Evaluate a score for each bacterial taxa of the plurality of bacterial taxa for producing a set of neuroactive compounds, wherein the set of neuroactive compounds are compounds which influences the functioning of a gut-brain axis and wherein the score is evaluated independently for each compound of the set of neuroactive compounds and stored in a bacteria- function matrix — 312

Calculate a metabolic potential (MP) corresponding to each compound of the set of neuroactive compounds using the bacteria function matrix and the scaled bacterial abundance values, wherein the metabolic potential (MP) is indicative of the capability of the bacterial community for producing the neuroactive compound — 314

Generate a classification model utilizing the metabolic potential (MP) of each compound of the set of neuroactive compounds using machine learning techniques — 316

Predict the risk of the person to develop or suffering from ASD in a significant, a low or no risk, using the classification model based on a predefined set of conditions — 318

Design therapeutic approaches, through targeting the bacterial groups that are capable of producing a set of neurotoxic compounds or facilitating growth of healthy microbes (including those producing neuro-protective compounds), wherein the set of neurotoxic compounds are compounds which negatively affects the functioning of the gut-brain axis — 320

SYSTEM AND METHOD FOR RISK ASSESSMENT OF AUTISM SPECTRUM DISORDER

PRIORITY CLAIM

The present application is a U.S. National Stage Filing under 35 U.S.C. § 371 and claims priority from International Application No. PCT/IB2020/057397, filed on Aug. 5, 2020, which application claims priority from Indian Patent Application No. 201921031560, filed on Aug. 5, 2019. The entire contents of the aforementioned applications are incorporated herein by reference.

TECHNICAL FIELD

The embodiments herein generally relate to the field of autism spectrum disorder (ASD), and, more particularly, to a method and system for assessing the risk of an individual for autism spectrum disorder using the metabolic potential of the resident gut bacteria.

BACKGROUND

Autism Spectrum Disorder (ASD) is a neurological and developmental disorder that impacts behaviour and social communication of an individual. ASD covers a wide array of conditions with varied symptoms and severity. Some of the primary symptoms include difficulty in communication, restricted interest, repetitive behaviour, making little or inconsistent eye contact etc. ASD is categorized as a developmental disorder as the symptoms usually appear at the childhood (around the age of 2 years). In case of high-functioning ASD with mild challenges, symptoms may emerge at an adult age. ASD, at the current scenario, is not curable, but early treatment can potentially improve the quality of a child's life. A wide variety of treatment strategies are adopted in practice based on the type/severity of the disease which may include behavioural, psychological, and/ or educational interventions.

An early diagnosis/risk-assessment of ASD would aid in designing better disease management schemes which in turn, may help improving the lifestyle of an individual suffering from the disorder. Diagnosing autism spectrum disorder (ASD) can be difficult, since there is no medical test, to diagnose the disorders. Doctors look at the patient's (normally children) behaviour and development to make a diagnosis. However, many children do not receive a final diagnosis until much older. This delay means that children with an ASD might not get the help they need. The diagnosis of ASD has been reported to be difficult in children of age less than four years due to primarily incomplete speech development.

The microbial community residing on and within human body is increasingly being acknowledged for its role in health and disease. Disruption in the healthy composition of the microbial community is referred to as dysbiotic condition. A wide range of studies have indicated association between the microbial cohort in the gastrointestinal tract (gut) (which constitutes a major portion of the total resident microbiome) and the etiology of diseases (or disorders) like diabetes, obesity, colorectal cancer (CRC), inflammatory bowel disease (IBD). Alterations in microbial community composition has also been reported in fecal and intestinal tissue samples obtained from ASD patients compared to those obtained from healthy individuals.

SUMMARY

Embodiments of the present disclosure present technological improvements as solutions to one or more of the above-mentioned technical problems recognized by the inventors in conventional systems. For example, in one embodiment, a system for risk assessment of autism spectrum disorder (ASD) in a person has been provided. The system comprises a sample collection module, a DNA extractor, a sequencer, one or more hardware processors, and a memory. The sample collection module obtains a sample from a body site of the person. The DNA extractor extracts Deoxyribonucleic Acid (DNA) from the obtained sample. The sequencer sequences the isolated DNA using a sequencer to obtain stretches of DNA sequences. The memory in communication with the one or more hardware processors, wherein the one or more first hardware processors are configured to execute programmed instructions stored in the memory, to: analyze the stretches of DNA sequences to identify a plurality of bacterial taxa present in the sample, wherein the analysis results in the generation of a bacterial abundance profile having a bacterial abundance value of each of the plurality of bacterial taxa in the sample; pre-process the bacterial abundance profile to obtain scaled bacterial abundance values of the bacterial abundance profile; evaluate a score for each bacterial taxa of the plurality of bacterial taxa for producing a set of neuroactive compounds, wherein the set of neuroactive compounds are compounds which influences the functioning of a gut-brain axis and wherein the score is evaluated independently for each compound of the set of neuroactive compounds and stored in a bacteria-function matrix; calculate a metabolic potential (MP) corresponding to each compound of the set of neuroactive compounds using the bacteria function matrix and the scaled bacterial abundance values, wherein the metabolic potential (MP) is indicative of the capability of the bacterial community for producing the neuroactive compound; generate a classification model utilizing the metabolic potential (MP) of each compound of the set of neuroactive compounds using machine learning techniques; predict the risk of the person to develop or suffering from ASD in a significant risk, a low risk or no risk, using the classification model based on a predefined set of conditions; and design therapeutic approaches, through targeting the bacterial groups that are capable of producing a set of neurotoxic compounds or facilitating growth of healthy microbes, wherein the set of neurotoxic compounds are compounds which negatively affects the functioning of the gut-brain axis.

In another aspect, a method for risk assessment of autism spectrum disorder (ASD) in an individual has been provided. Initially, a sample is obtained from a body site of the person. The obtained sample is then used to extract Deoxyribonucleic Acid (DNA). In the next step, the isolated DNA is sequenced using a sequencer to obtain stretches of DNA sequences. Further, the stretches of DNA sequences are analyzed to identify a plurality of bacterial taxa present in the sample, wherein the analysis results in the generation of a bacterial abundance profile having a bacterial abundance value of each of the plurality of bacterial taxa in the sample. Further, the bacterial abundance profile is pre-processed to obtain scaled bacterial abundance values of the bacterial abundance profile. In the next step, a score is evaluated for each bacterial taxa of the plurality of bacterial taxa for producing a set of neuroactive compounds, wherein the set of neuroactive compounds are compounds which influence the functioning of a gut-brain axis and wherein the score is evaluated independently for each compound of the set of neuroactive compounds and stored in a bacteria-function matrix. Further, a metabolic potential (MP) is calculated corresponding to each compound of the set of neuroactive compounds using the bacteria function matrix and the scaled bacterial abundance values, wherein the metabolic potential (MP) is indicative of the capability of the bacterial community for producing the neuroactive compound. Further, a classification model is generated utilizing the metabolic potential (MP) of each compound of the set of neuroactive compounds using machine learning techniques. Later, the risk of the person to develop or suffering from ASD in a significant risk, a low risk or no risk, is predicted using the classification model based on a predefined set of conditions. And finally, therapeutic approaches are designed, through targeting the bacterial groups that are capable of producing a set of neurotoxic compounds or facilitating growth of healthy microbes, wherein the set of neurotoxic compounds are compounds which negatively affects the functioning of the gut-brain axis.

In yet another aspect, one or more non-transitory machine readable information storage mediums comprising one or more instructions which when executed by one or more hardware processors cause risk assessment of autism spectrum disorder (ASD) in an individual. Initially, a sample is obtained from a body site of the person. The obtained sample is then used to extract Deoxyribonucleic Acid (DNA). In the next step, the isolated DNA is sequenced using a sequencer to obtain stretches of DNA sequences. Further, the stretches of DNA sequences are analyzed to identify a plurality of bacterial taxa present in the sample, wherein the analysis results in the generation of a bacterial abundance profile having a bacterial abundance value of each of the plurality of bacterial taxa in the sample. Further, the bacterial abundance profile is pre-processed to obtain scaled bacterial abundance values of the bacterial abundance profile. In the next step, a score is evaluated for each bacterial taxa of the plurality of bacterial taxa for producing a set of neuroactive compounds, wherein the set of neuroactive compounds are compounds which influence the functioning of a gut-brain axis and wherein the score is evaluated independently for each compound of the set of neuroactive compounds and stored in a bacteria-function matrix. Further, a metabolic potential (MP) is calculated corresponding to each compound of the set of neuroactive compounds using the bacteria function matrix and the scaled bacterial abundance values, wherein the metabolic potential (MP) is indicative of the capability of the bacterial community for producing the neuroactive compound. Further, a classification model is generated utilizing the metabolic potential (MP) of each compound of the set of neuroactive compounds using machine learning techniques. Later, the risk of the person to develop or suffering from ASD in a significant risk, a low risk or no risk, is predicted using the classification model based on a predefined set of conditions. And finally, therapeutic approaches are designed, through targeting the bacterial groups that are capable of producing a set of neurotoxic compounds or facilitating growth of healthy microbes, wherein the set of neurotoxic compounds are compounds which negatively affects the functioning of the gut-brain axis.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles:

FIG. 3 is a flowchart illustrating the steps involved in risk assessment of an individual for autism spectrum disorder according to an embodiment of the present disclosure.

DETAILED DESCRIPTION OF THE EMBODIMENTS

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

Glossary—Terms Used in the Embodiments

The expression "microbiome" or "microbial genome" in the context of the present disclosure refers to the collection of genetic material of a community of microorganism that inhabit a particular niche, like the human gastrointestinal tract.

The expression "neuroactive compound" in the context of the present disclosure refers to the compounds that have the capability to regulate/interfere with neurotransmission, thus affecting brain function.

Figure 1:
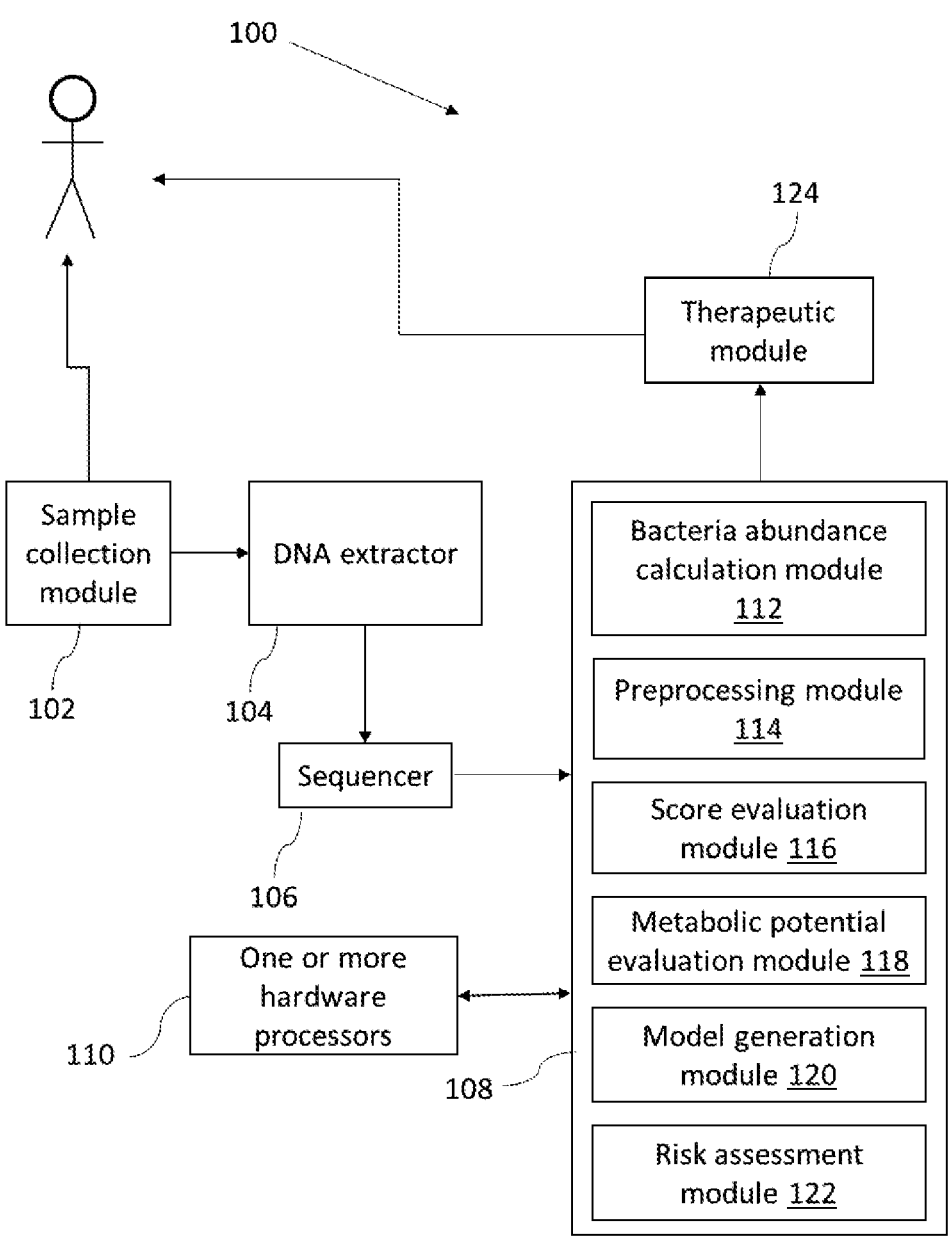
FIG. 1 illustrates a block diagram of a system for risk assessment of an individual for autism spectrum disorder according to an embodiment of the present disclosure.

Referring now to the drawings, and more particularly to FIG. 1 and FIG. 3, where similar reference characters denote corresponding features consistently throughout the figures, there are shown preferred embodiments and these embodiments are described in the context of the following exemplary system and/or method.

According to an embodiment of the disclosure, a system 100 for risk assessment of an individual for autism spectrum disorder (ASD) is shown in the block diagram of FIG. 1. The system 100 is using a non-invasive method for risk assessment of the individual, especially children, for ASD through prediction of metabolic potential of the bacteria residing in gastrointestinal tract (gut) of the individual. It should be appreciated that the other microbes in the gut can also be considered for the diagnosis and risk assessment of the individual for ASD. Further, the present disclosure also provides bacterial community based therapeutic approaches that can potentially minimize the side effects through maintaining the healthy cohort of bacteria in gut.

The system 100 is configured to calculate a score, named as 'SCORBPEO' (Score for Bacterial Production of Neuroactive Compounds) is evaluated from the gut bacterial community's taxonomic abundance profile, which is indicative of its metabolic potential for production of a particular neuroactive compound. This score is subsequently used to predict the probability of the individual for ASD. The individual here may be referred as a child, though the individual may also be an adult. Since the scheme proposed in the present disclosure doesn't rely on the behavioural aspects of the child, it can potentially be an effective component of ASD diagnosis process in children of age less than four years. Given the asymptomatic nature of the disease, the proposed non-invasive approach, if included as a part of routine health screening measures of an individual, can potentially help in early diagnosis of the ASD. The system 100, in addition, entails therapeutic regimes through targeting the bacterial groups (residing in gut) that are capable of producing neurotoxic compounds or facilitating growth of healthy microbes (including those producing neuro-protective compounds), wherein neuro-protective compounds refer to the compounds which positively affect the functioning of gut-brain axis.

In the present disclosure, a set of metabolic pathways harboured by the bacterial community residing in gut has been utilized to develop an ASD diagnosis scheme that, when applied with the conventional screening tests, may help in early diagnosis of the ASD. The set of metabolic pathways utilized in the current invention pertain to degradation of tryptophan leading to production of neuro-active compounds. Since, the microbiome's metabolic repertoire is a deeper reflector of the host-microbiome interplay than only the taxonomic groups, analysis of metabolomics of the resident microbiome is increasingly being acknowledged for understanding 'disease-microbiome' association.

According to an embodiment of the disclosure, the system 100 consists of a sample collection module 102, a DNA extractor 104, a sequencer 106, a memory 108 and a processor 110 as shown in FIG. 1. The processor 110 is in communication with the memory 108. The processor 110 is configured to execute a plurality of algorithms stored in the memory 108. The memory 108 further includes a plurality of modules for performing various functions. The memory 108 may include a bacterial abundance calculation module 112, a pre-processing module 114, a score evaluation module 116, a metabolic potential (MP) evaluation module 118, a model generation module 120 and a diagnosis/risk assessment module 122. The system 100 further comprises a therapeutic module 124 as shown in the block diagram of FIG. 1.

According to an embodiment of the disclosure, the bacterial sample is collected using the sample collection module 102. The sample collection module 102 is configured to obtain a sample from a body site of the individual. Normally, the sample is collected in the form of saliva/stool/blood/tissue/other body fluids/swabs from at least one body site/location viz. gut, oral, skin, urinogenital tract etc.

The system 100 further comprises the DNA (Deoxyribonucleic acid) extractor 104 and the sequencer 106. DNA is first extracted from the microbial cells constituting the bacterial sample using laboratory standardized protocols by employing the DNA extractor 104. DNA isolation process using standard protocols based on the isolation kits (like Norgen, Purelink, OMNI gene/Epicentre etc.). Next, sequencing of the bacterial DNA is performed using the sequencer 106. The extracted bacterial DNA, after purification is subjected to NGS (Next Generation Sequencing) technology for generating human readable form of short stretches of DNA sequence called reads. The said NGS technology involves amplicon sequencing targeting bacterial marker genes (such as 16S rRNA, 23S rRNA, rpoB, cpn60 etc.). The sequence reads, thus obtained, are computationally analysed through widely accepted standard frameworks for NGS data analysis. In another embodiment, the sequencer 106 may involve Whole Genome Sequencing (WGS) where the reads are generated for the total DNA content of a given sample. In yet another embodiment, the set of microbial genes involved in the production of the neuroactive compounds (under the current invention) may be sequenced using targeted PCR (Polymerase Chain Reaction). In yet another implementation, RNA-seq. technology may be used to sequence the microbial RNA (Ribonucleic acid) content of a given sample. This can be performed targeting the whole bacterial RNA content or a particular set of RNAs. RNA-seq provides insights into the active genes in a sample. In the current invention, RNA-seq may be performed targeting the microbial RNAs (or transcripts) corresponding to the set of genes. The extracted and sequenced DNA sequences are then provided to the processor 110.

According to an embodiment of the disclosure, the system 100 further comprises the bacterial abundance calculation module 112. The bacterial abundance calculation module 112 is configured to analyze the stretches of DNA sequences to identify a plurality of bacterial taxa present in the sample, wherein the analysis results in the generation of a bacterial abundance profile having a bacterial abundance value of each of the plurality of bacterial taxa in the sample. The generation of bacterial abundance profile involves computationally analyzing one or more of a microscopic imaging data, a flow cytometry data, a colony count and cellular phenotypic data of microbes grown in in-vitro cultures, a signal intensity data, wherein these data are obtained by applying one or more of techniques including culture dependent methods, one or more of enzymatic or fluorescence assays, one or more of assays involving spectroscopic identification and screening of signals from complex microbial populations In an example, the bacterial abundance profile is generated, though it should be appreciated that the bacterial abundance module 112 is not limited to only bacteria in the gut, other microbes in the gut can also be considered for analysis. The bacterial abundance calculation module 112 utilizes widely accepted methods/similar frameworks for calculation of abundance profile. The raw abundance profile, thus obtained, is further processed to obtain the relative abundance (RA) of each of the bacterial taxa, wherein taxa or taxon refers to individual taxonomic groups. Each characterized microbe from the sample can be associated to a taxonomic group. The methodology for calculation of relative abundance (RA) has been provided in the later part of the disclosure. In the present disclosure, the abundances of the bacterial groups at the taxonomic level of 'genus' have been considered. It should be appreciated that in another embodiment, other microbes in the gut can also be considered for diagnosis and risk assessment of the individual for ASD. In another embodiment, the abundances of bacterial groups corresponding to other taxonomic levels, such as, but not limited to, phylum, class, order, family, species, strain, OTUS (Operational Taxonomic Units), Asvs (Amplicon sequence variant) etc. may be considered.

According to an embodiment of the disclosure, the system 100 also comprises the pre-processing module 114. The pre-processing module is configured to pre-process the bacterial abundance profile to obtain normalized/scaled bacterial abundance values of the bacterial abundance profile. The pre-processing of the microbial abundance data comprises normalizing to represent the abundance in form of scaled values, wherein the normalization on microbial counts is performed through one or more of a rarefaction, a quantile scaling, a percentile scaling, a cumulative sum scaling or an Aitchison's log-ratio transformation.

Figure 2:
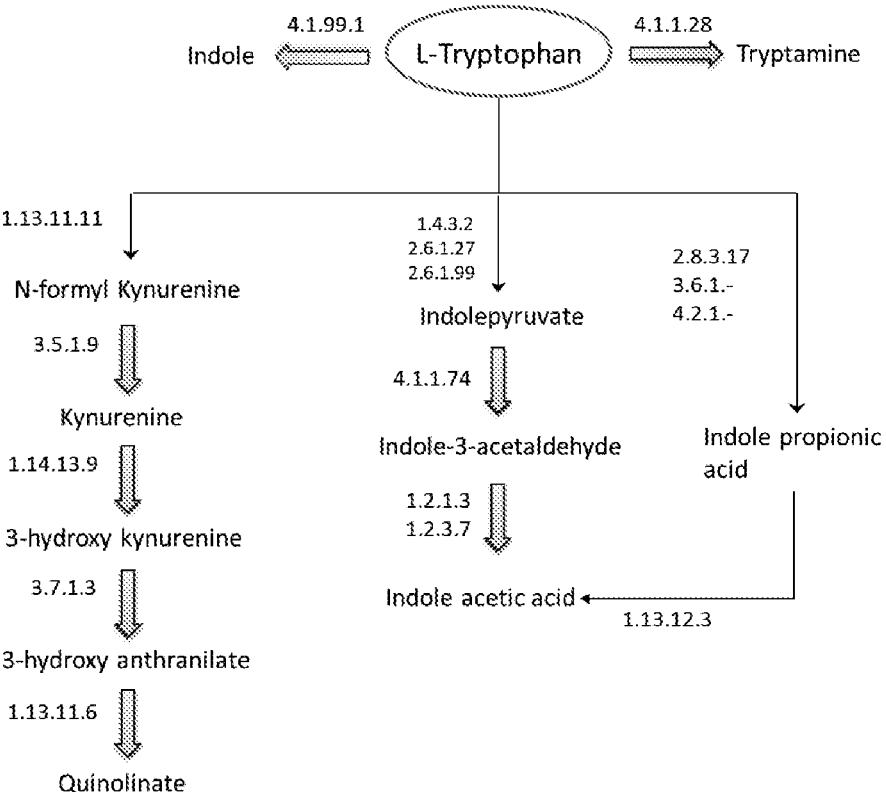
FIG. 2 depicts the biochemical pathways for production of the six neuroactive compounds in bacteria according to an embodiment of the disclosure.

According to an embodiment of the disclosure, the system 100 further comprises the score evaluation module 116. The score evaluation module 116 is configured evaluate a score for each bacterial taxa of the plurality of bacterial taxa for producing a set of neuroactive compounds, wherein the set of neuroactive compounds are compounds which influences the functioning of a gut-brain axis and wherein the score is evaluated independently for each compound of the set of neuroactive compounds and stored in a bacteria-function matrix. The gut-brain axis (GBA) refers to a bi-directional link between the central nervous system (CNS) and the enteric nervous system (ENS). The GBA enables communication of emotional and cognitive centres of the brain with peripheral intestinal functions. This communication primarily involves neural, endocrine and immune pathways. The score evaluation module 116 may also utilize any other microorganism for the evaluation of score. It should be appreciated that the bacteria-function matrix can also be made using other microorganisms in the gut. In an example, the score can be referred as the "SCORBPEO (Score for Bacterial Production of Neuroactive Compounds)" value. The set of neuroactive compounds include (but not limited to) Kynurenine, Quinolinate, Indole, Indole Acetic Acid (IAA), Indole propionic acid (IPA) and Tryptamine. The biochemical pathways for production of these six compounds (through tryptophan utilization) in bacteria are depicted in FIG. 2.

The 'SCORBPEO (Score for Bacterial Production of Neuroactive Compounds)' value for a particular neuroactive compound 'i' corresponding to a bacterial genus 'j', was calculated using the equation (1)

$$SCORBPEO_{ij} = P * \alpha * \beta \qquad (1)$$

where P represents the proportion of strains belonging to the genus 'j' that have been predicted with compound 'i' producing capability (value of P ranges between '0' and '1'). Prediction of compound 'i' producing capability involves computational identification of the enzymes (proteins) involved in conversion of tryptophan to compound 'i'. Identification of enzymes was performed using widely accepted tools/packages (such as, but not limited to, Blast, HMMER, Pfam, etc.) which employ protein sequence/functional domain similarity search algorithms. Further, in order to increase the prediction efficiency, a filtration step was included (wherever applicable) based on presence of the genes/functional domains (of a particular pathway) in proximity to each other in the genome of a particular organism.

α denotes a confidence value of the corresponding bacterial group. In an embodiment, the value of a ranges between '1' and '10'. It should be appreciated that the value may vary in another embodiments.

β corresponds to a 'gut weightage' which represents an enrichment value of a particular pathway in the gut environment. In an embodiment, the value of β ranges between '1' and '5'. It should be appreciated that the value may vary in another embodiments. This value is calculated considering the number of gut-strains with capability of producing 'i' as compared to the number of corresponding non-gut strains.

In another example, computational identification of enzymes can also be performed using any one or a combination of gene/protein sequence similarity search algorithms, gene' protein sequence composition based algorithms, protein domain/motif similarity search algorithms, protein structure similarity search algorithms. The enzymes, thus obtained, may further be filtered using any one or a combination of genomic proximity analysis, functional association analysis, catalytic site analysis, sub-cellular localization prediction and secretion signal prediction. Further, identification of enzyme can also be performed using lab experiments which involves enzyme characterization assays.

According to an embodiment of the disclosure, the memory 108 further comprises the metabolic potential (MP) evaluation module 118. The metabolic potential evaluation module 118 is configured to predict the metabolic potential for each of the neuroactive compounds using the bacteria function matrix and the normalized abundance values, wherein the metabolic potential is indicative of the capability of the bacterial community (derived from the sequence data of the extracted DNA) for producing the neuroactive compound. The set of neuroactive compounds include (but not limited to) Kynurenine, Quinolinate, Indole, Indole Acetic Acid (IAA), Indole propionic acid (IPA), and Tryptamine. The metabolic potential (MP) for production of a particular metabolite (by the bacterial community of interest) is calculated based on—(i) the relative abundance of the bacterial genera predicted to have the corresponding metabolic pathway and (ii) a predefined score referred to as (in the current invention) 'SCORBPEO' which represents the potential of a particular genus for production of the metabolite. Thus, the MP for production of a particular metabolite by the bacterial community (of interest) can be written as follows in equation (2). The equation (2) has been provided for the calculation of metabolic potential (MP) for Kynurenine.

$$MP_{Kyn} = \sum_{i=1}^{n} RA_i \times SCORBPEO_{[Kyn][i]} \qquad (2)$$

Where, $MP_{Kyn}$—Metabolic potential of the bacterial community of interest for the production of Kynurenine. The bacterial community, in the current invention, may indicate the one isolated from the gut sample of the individual.

n—Number of Kynurenine producing bacterial genera present in the bacterial community of interest. This number is acquired from the predefined 'bacteria-function matrix'. The methodology followed for construction of the 'bacteria-function matrix' has been explained in the later part of the disclosure with the help of experimental study.

RA—Relative abundance of a particular bacterial genus predicted to have the metabolic pathway for Kynurenine production. The 'RA' is calculated using the pre-processing module 114 as described above.

$SCORBPEO_{[Kyn][i]}$—The potential of genus 'i' for production of Kynurenine as explained earlier 'SCORBPEO' score or any other score related to microbial production of any other products/by-products of amino acid metabolism (apart from the above mentioned six compounds) for risk assessment/diagnosis/therapeutics of ASD (or any other neuro-developmental disease/disorder) are well within the scope of the present disclosure.

Thus, in the present embodiment, the MP is calculated for six neuroactive compounds, i.e. for Kynurenine, Quinolinate, Indole, Indole Acetic Acid (IAA), Indole propionic acid (IPA), and Tryptamine. These six 'MP' values are used further. In an example, the values of the computed MP scores ranges between 0 and 50. Though it should be appreciated that the range of MP values may vary in other examples. The values were further rescaled to '0-10'. For a particular pathway, a bacterial taxon having a higher MP would indicate a greater capability of production of a particular compound as compared to a taxon with a lower MP.

It should be appreciated that the MP score or any other score related to microbial production of any other products/by-products of amino acid metabolism (apart from the above mentioned six compounds) for risk assessment/diagnosis/therapeutics of ASD (or any other neurodegenerative disease/disorder) are well within the scope of the present disclosure.

According to an embodiment of the disclosure, the system 100 further comprises the model generation module 120. The model generation module 120 is configured to generate a classification model utilizing the MP of each of the plurality of compounds using a machine learning technique. The model generation module 120 builds the classification model for predicting the risk of the individual to be suffering from ASD. In an embodiment, the classification model is generated using machine learning techniques may be performed using one or more of classification algorithms which include decision trees, random forest, linear regression, logistic regression, naive Bayes, linear discriminant analyses, k-nearest neighbour algorithm, Support Vector Machines and Neural Networks.

The model for prediction of ASD is generated based on the MP (Metabolic potential) values corresponding to each of the six neuroactive compounds. These six compounds include Kynurenine, Quinolinate, Indole, Indole acetic acid (IAA), Indole propionic acid (IPA), and Tryptamine. The publicly available gut microbiome data (16SrRNA sequences) pertaining to ASD patients and matched healthy individuals was used to validate the efficiency of the ASD diagnosis and risk assessment scheme proposed in the present disclosure. For a child/person (of age 3-17 years) undergoing routine health check-up, especially those with genetic pre-disposition to the disorder, the prediction outcome of the current module indicates the risk of disease development. For another category of individuals with one or more of the associated symptoms, the current module can be used as a non-invasive diagnostic measure as an adjunct to the behavioural screening i.e. commonly practiced.

According to an embodiment of the disclosure, the system 100 also comprises the risk assessment module 122. The risk assessment module 122 is configured to predict the risk of the individual to develop or suffering from ASD in a significant risk, a low risk or no risk, using the classification model based on a predefined set of conditions. The prediction outcome of the risk assessment module 122 indicates the probability of having the disease or the risk of disease development. For another category of individuals with one or more of the behavioural symptoms of ASD, the risk assessment module 122 can be used as an initial non-invasive diagnostic measure.

The predefined set of condition comprises comparing the metabolic potential for production of one of the set of neuroactive compounds with a threshold value, wherein the result of comparison is: no risk of ASD if the metabolic potential is less than the threshold value, the low risk if the metabolic potential is between the threshold value and a third quartile value of a data set containing the metabolic potential values of the neuroactive compound, and the significant risk if the metabolic potential is more than the third quartile value of a data set containing the metabolic potential values of the neuroactive compound.

According to an embodiment of the disclosure, the system 100 also comprises the therapeutic module 124. The therapeutic module 124 is configured to design therapeutic approaches through targeting the bacterial groups that are capable of producing a set of neurotoxic compounds or facilitating growth of healthy microbes, wherein the set of neurotoxic compounds are compounds which negatively affects the functioning of the gut-brain axis. The therapeutic intervention is provided to the individual wherein the symptoms of ASD may be alleviated through minimizing the side effects of conventional therapies through maintaining a 'healthy' microbiome.

The therapeutic module 124 involves identification of a consortium of microbes which can be used (in form of pre-/probiotic/synbiotic) in order to—(i) reduce the growth of bacteria (in the gut) which are capable of producing neurotoxic compounds and (ii) enhance the growth of beneficial bacteria (in the gut) which can help maintaining a healthy gut or produce neuroactive compounds which are beneficial for functioning and regulation of gut-brain axis. This consortium of microbes can be administered either alone or as an adjunct to the conventional antibiotic drugs for improved treatment of ASD and also the gastrointestinal problems associated to ASD. In the present embodiment, identification of the consortium of bacteria is performed based on the SCORBPEO values of the bacterial genera identified in a particular sample. Though it should be appreciated that the MP values of other microorganisms can also be considered.

The identification of consortium of bacteria that can potentially facilitate improved therapy of Autism Spectrum Disorder (ASD) was performed based on the following two aspects—(i) differentially abundant bacterial taxa in cohorts of Autism patients and healthy individuals (The microbiome data provided in one of the research paper has been considered as a case study) and (ii) the 'SCORBPEO' values of the differentially abundant taxa corresponding to the production of neuroactive compounds under the current disclosure.

The abundant genera in healthy cohort which are not able to produce any neurotoxic compound may help maintaining a 'healthy' microbiome in gut and thus might aid in prevention or alleviating symptoms of ASD. These genera are listed in TABLE 1. Any pre/probiotic/synbiotic formulation which facilitates growth of the above mentioned healthy microbiome can also be used as a therapeutic adjunct for ASD. The differentially abundant taxa (genera in the current disclosure) in healthy cohort were identified using state-of-art statistical test.

TABLE 1

List of genera helpful in maintaining the healthy microbiome in the gut

| Genera | P-value |
|---|---|
| *Eubacterium* | 0.003 |
| *Parvimonas* | 0.029 |
| *Paraprevotella* | 0.045 |
| *Clostridium_XIVa* | 0.019 |

The proposed probiotic formulation may be composed of bacterial strains belonging to the genera listed in Table 1. The strains with known beneficial effects (like butyrate production etc.) are most probable candidates for probiotic formulation. For example, certain strains under the genera *Eubacterium* and *Clostridium* XIVa have been reported to have beneficial role in the gut. Thus, these strains may be provided as probiotic formulation in order to maintain a healthier gut microbiome, thus improving the efficiency of current therapeutic approaches or minimizing the side effects of the conventional therapies of ASD. The bacterial strains belonging to the genera *Eubacterium* and *Clostridium* XIVa that are commonly found in gut, are listed in TABLE 2.

TABLE 2

Bacterial strains belonging to the genera *Eubacterium* and *Clostridium* XIVa, which are commonly found in gut

| Genus | Strain |
|---|---|
| *Eubacterium* | *Eubacteriumbiforme* DSM 3989 |
| | *Eubacteriumcylindroides* ATCC 27803 |
| | *Eubacteriumcylindroides* T2-87 |
| | *Eubacteriumdolichum* DSM 3991 |
| | *Eubacteriumhallii* DSM 3353 |
| | *Eubacteriumhallii* SM6/1 |
| | *Eubacteriuminfirmum* CD1_FAA_NB_6 |
| | *Eubacteriumramulus* ATCC 29099 |
| | *Eubacteriumrectale* |
| | *Eubacteriumrectale* DSM 17629 |
| | *Eubacteriumsiraeum* |
| | *Eubacteriumsiraeum* DSM 15702 |
| | *Eubacteriumsiraeum* V10Sc8a |
| | *Eubacterium* sp. HMP2021 |
| | *Eubacterium* sp. HMP2025 |
| | *Eubacterium* sp. HMP2027 |
| | *Eubacterium* sp. HMP2029 |
| | *Eubacterium* sp. L2-7 |
| | *Eubacteriumventriosum* ATCC 27560 |
| *Clostridium_XIVa* | *Clostridium symbiosum* ATCC 14940 |
| | *Clostridium symbiosum* WAL-14163 |
| | *Clostridium symbiosum* WAL-14673 |
| | *Clostridium nexile* DSM 1787 |
| | *Coprococcuseutactus* ATCC 27759 |

In operation, a flowchart 300 illustrating the steps involved for combating. Initially at step 302, the sample is obtained from a body site of the individual. At step 304, the DNA is extracted from the obtained sample. At step 306, the obtained sample is then sequencing the isolated DNA using the sequencer * to obtain stretches of DNA sequences. At step 308, the stretches of DNA sequences are analyzed to identify a plurality of bacterial taxa present in the sample. The analysis results in the generation of a bacterial abundance profile having a bacterial abundance value of each of the plurality of bacterial taxa in the sample.

At step 310, the bacterial abundance profile is pre-processed to obtain normalized/scaled bacterial abundance values of the bacterial abundance profile. Further at step 312, the score such as SCORBPEO is evaluates for each bacterial taxa of the plurality of bacterial taxa for producing a set of neuroactive compounds. The set of neuroactive compounds are compounds which influences the functioning of a gut-brain axis and wherein the score is evaluated independently for each compound of the set of neuroactive compounds and stored in a bacteria-function matrix;

At step 314, the metabolic potential (MP) is calculated corresponding to each compound of the set of neuroactive compounds using the bacteria function matrix and the scaled bacterial abundance values. The metabolic potential (MP) is indicative of the capability of the bacterial community for producing the neuroactive compound. Further at step 316, the classification model is generated by utilizing the metabolic potential (MP) of each compound of the set of neuroactive compounds using machine learning techniques. In an embodiment, the classification model is generated using machine learning techniques may be performed using one or more of classification algorithms which include decision trees, random forest, linear regression, logistic regression, naive Bayes, linear discriminant analyses, k-nearest neighbour algorithm, Support Vector Machines and Neural Networks.

At step 318, the risk of the individual to develop or suffering from ASD is predicted. The prediction says about the individual to in one of a significant risk, a low risk or no risk, using the classification model based on a predefined set of conditions. And finally at step 320, a therapeutic approach is designed, through targeting the bacterial groups that are capable of producing a set of neurotoxic compounds or facilitating growth of healthy microbes, wherein the set of neurotoxic compounds are compounds which negatively affects the functioning of the gut-brain axis.

According to an embodiment of the disclosure, the system 100 for risk assessment of autism spectrum disorder (ASD) in the individual can also be explained with the help of following example.

The prediction of the bacterial community metabolic potential for the production of neuroactive compounds requires the (bacterial) taxonomic abundance data, generated using one of the state-of-art algorithms, as an input. An example of the bacterial taxonomic abundance data (obtained from a published study) has been shown below in TABLE 3. Bacterial community data pertaining to a total of 30 Autism samples and corresponding 24 healthy samples are provided in the study. TABLE 3 shows a subset of the taxonomic abundance at genera level corresponding to one autism and one healthy sample.

TABLE 3

Subset of genera abundance obtained through analyzing gut bacterial community data corresponding to an autistic child and a healthy child

| Taxa | Autism Sample | Control Sample |
|---|---|---|
| *Bacteroides* | 27686 | 141 |
| *Prevotella* | 214004 | 443508 |
| *Comamonas* | 121 | 0 |
| *Alistipes* | 6031 | 29 |
| *Staphylococcus* | 6 | 19 |
| *Parabacteroides* | 4026 | 21 |
| *Faecalibacterium* | 25035 | 35305 |
| *Ruminococcus* | 593 | 98 |

The raw abundance data was then normalized to represent the relative abundance values as shown in TABLE 4. It should be noted that any kind of normalization or scaling of bacterial abundance values, including percentage, cumulative sum scaling, minmax scaling, maxAbs scaling, robust scaling, percentile, quantile, Atkinson's log transformation, etc., can be employed. Such representation provides an easy interpretation of the relative contribution of each taxa in the total bacterial abundance in a sample.

TABLE 4

Normalized values of the abundances shown in TABLE 3

| Taxa | Autism Sample | Control Sample |
|---|---|---|
| *Bacteroides* | 0.079 | 0.0002 |
| *Prevotella* | 0.612 | 0.878 |
| *Comamonas* | 0.0003 | 0 |
| *Alistipes* | 0.017 | 0.00005 |
| *Staphylococcus* | 0.00001 | 0.00003 |
| *Parabacteroides* | 0.011 | 0.00004 |
| *Faecalibacterium* | 0.071 | 0.069 |
| *Ruminococcus* | 0.001 | 0.0001 |

The normalized abundance values were then used to evaluate the score referred to as 'Metabolic potential (MP)' in the present disclosure. This score indicates the bacterial community's capability for production of a particular neuroactive compound. The present invention includes 'MP' scores for six compounds belonging to tryptophan metabolism. These six compounds include Kynurenine, Quinolinate, Indole, Indole acetic acid (IAA), Indole propionic acid (IPA) and Tryptamine. These compounds have been reported to affect neurological functions through direct or indirect routes. 'MP' score or any other score related to microbial production of any other products/by-products of amino acid metabolism (apart from the above mentioned six compounds) for risk assessment/diagnosis/therapeutics of autism are well within the scope of the present invention.

A model for diagnosis and risk assessment of Autism is generated based on the 'Metabolic potential (MP)' values corresponding to each of the six neuroactive compounds. The evaluation of 'MP' values has been described in the above paragraph. These six compounds include Kynurenine, Quinolinate, Indole, Indole acetic acid (IAA), Indole propionic acid (IPA), and Tryptamine. 'MP' score or any other score related to microbial production of any other products/by-products of amino acid metabolism (apart from the above mentioned six compounds) for risk assessment/diagnosis/therapeutics of autism or any other neurodevelopmental disorder are well within the scope of the present invention.

The publicly available gut microbiome datasets (16S sequence) pertaining to autism patients and matched healthy controls were used to validate the efficiency of the Autism risk assessment scheme proposed in the present disclosure. A summary on the dataset used is provided in TABLE 5.

TABLE 5

| Summary of the publicly available dataset used for validation of the proposed methodology | | | | |
|---|---|---|---|---|
| Sample type | Data type | No. of Autism patients | No. of healthy individuals | Reference |
| Fecal sample | 16S rRNA sequence read | 30 | 24 | Pulikkanet al. 2018 |

The dataset involves publicly available gut microbiome sequence data samples from 30 individuals suffering from Autism and corresponding 24 healthy controls from Indian population. The 16S rRNA data from the study was analyzed in order to obtain the 'MP' values for the six neuroactive compounds under the invention. These values corresponding to a subset of samples from the study is provided in TABLE 6.

TABLE 6

| 'Metabolic potential (MP)' values corresponding to the six neuro-active compounds evaluated for a subset of samples mentioned from the study. | | | | | |
|---|---|---|---|---|---|
| | MP values of six neuro-active compounds | | | | |
| | Kynurenine | Quinolinate | Indole | Indole acetic acid (IAA) | Indole propionic acid (IPA) | Tryptamine |
| Autism_1 | 0.0124 | 0.1411 | 0.1435 | 0 | 0.2688 | 0.5454 |
| Autism_2 | 0.0405 | 0.0033 | 0.0250 | 0.0001 | 2.2594 | 0.9563 |
| Healthy_1 | 0.0003 | 0.0110 | 0.0270 | 0 | 0.5484 | 0.0940 |
| Healthy_2 | 0.0006 | 0.3906 | 0.3613 | 0 | 0.8085 | 0.5814 |

A model for classification (disease or healthy) of the samples was generated using state-of-art machine learning algorithm considering the six 'MP' values as the feature set for each of the sample. The classification was performed (on the total 54 samples as mentioned in Table 5) for 1000 iterations with randomly chosen 80% (from each of disease and healthy cohorts) of the samples as training set and the remaining 20% (from each of disease and healthy cohorts) as the test set in each iteration. The model sensitivity and specificity were used for choosing the best parameters that are able to classify diseased samples from healthy ones. Out of the six compounds (mentioned in Table 6), kynurenine was observed to be the best classifier for healthy and diseased samples as shown in TABLE 7.

TABLE 7

| Parameters showing model efficiency of binary classification based on the 'MP' values corresponding to Kynurenine | | | | | | | |
|---|---|---|---|---|---|---|---|
| Feature | Threshold used for testing (T) | Train sensitivity | Train specificity | Train accuracy | Test sensitivity | Test specificity | Test accuracy |
| Kynurenine | 0.005 | 75.41 | 79.26 | 77.15 | 68.63 | 71.74 | 70.04 |

The diagnosis and prediction of the risk of Autism could be performed based on the 'MP' value and a threshold value corresponding to the above-mentioned feature 'kynurenine' according to the following rules—

$MP_{Kynurenine} <= T$ indicates no risk of Autism or no Autism, where T is the threshold value (as mentioned in the above table).

$T <= MP_{Kynurenine} <= Q_3$, indicates a low risk of Autism or low probability of suffering from Autism, where $Q_3$ is the third quartile value of the data set containing $MP_{Kynurenine}$ values which is 0.013 in the current example.

$MP_{Kynurenine} > Q_3$ (0.013 in the current example) indicates significant risk of Autism or significant probability of suffering from Autism.

It may be noted that, the present disclosure primarily relies on the metabolic capability of the resident gut microbiota, which is known to differ in relation to not only the diseased state but also various other factors like dietary pattern, demography, lifestyle etc. Therefore, any other neuroactive compound(s) (or any other compound belonging to amino acid metabolism) either alone or in combination with one or more of Kynurenine, Quinolinate, Indole, Indole acetic acid, Indole propionic acid, and Tryptamine may prove to be efficient risk assessment factors for ASD or any other neuro-developmental disease/disorder for individuals from a different geography or/and of different ethnicity/lifestyle.

Further, details of the bacterial genes involved in the production of neuroactive compound in the present disclosure is shown in TABLE 8.

TABLE 8

| | Gene name | Enzyme Id | Functional domain (obtained from Pfam database) |
|---|---|---|---|
| Metabolic pathways | | | |
| Tryptophan –> Kynurenine | kynA | 1.13.11.11 | Trp_dioxygenase |
| | kynB | 3.5.1.9 | Cyclase |
| Tryptophan –>Quinolinate | kynA | 1.13.11.11 | Trp_dioxygenase |
| | kynB | 3.5.1.9 | Cyclase |
| | kmo | 1.14.13.9 | FAD_binding_3 |
| | kynU | 3.7.1.3 | Aminotran_5 |
| | HAAO | 1.13.11.6 | 3-HAO |
| Tryptophan –> Indole | TnaA | 4.1.99.1 | Beta_elim_lyase |
| Tryptophan –> Indole acetic acid | ipdC | 4.1.1.74 | TPP_enzyme_C |
| | | | TPP_enzyme_M |
| | | | TPP_enzyme_N |
| | aldh | 1.2.1.3 | Aldedh |
| | AAO1 | 1.2.3.7 | Ald_Xan_dh_C |
| | | | Ald_Xan_dh_C2 |
| | iaaM | 1.13.12.3 | Amino_oxidase |
| Tryptophan –> Indole propionic acid | fldL | NA | AMP_binding |
| | | | AMP_binding_C |
| | fldA | 2.8.3.17 | CoA_transf_3 |
| | fldI | 3.6.1.- | BcrAD_BadFG |
| | fldB | 4.2.1.- | HGD-D |
| | fldC | 4.2.1.- | HGD-D |
| Tryptophan –>Tryptamine | ddc | 4.1.1.28 | Pyridoxal_deC |

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The embodiments of present disclosure herein address unresolved problem of early diagnosis of the ASD, especially in child. The embodiment provides a system and method for risk assessment of autism spectrum disorder (ASD) in an individual.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to per- form steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

The invention claimed is:

1. A method for risk assessment of autism spectrum disorder (ASD) in a person, the method comprising:

obtaining a sample from a body site of the person;

extracting Deoxyribonucleic Acid (DNA) from the obtained sample to obtain isolated DNA;

sequencing the isolated DNA using a sequencer to obtain stretches of DNA sequences;

analyzing, via one or more hardware processors, the stretches of DNA sequences to identify a plurality of bacterial taxa present in the sample, wherein the analysis results in the generation of a bacterial abundance profile having a bacterial abundance value of each of the plurality of bacterial taxa in the sample;

pre-processing, via the one or more hardware processors, the bacterial abundance profile to obtain scaled bacterial abundance values of the bacterial abundance profile;

evaluating, via the one or more hardware processors, a score for each bacterial taxon of the plurality of bacterial taxa for producing a set of neuroactive compounds, wherein the set of neuroactive compounds are compounds which influences the functioning of a gut-brain axis and wherein the score is evaluated independently for each compound of the set of neuroactive compounds and stored in a bacteria-function matrix, wherein the score (SCORBPEO) is calculated using formula:

$$SCORBPEO_{ij} = P * \alpha * \beta$$

where P—proportion of strains belonging to the genus 'j' that have been predicted with neuroactive compound 'i' producing capability, wherein prediction of the neuro-active compound 'i' producing capability involves computational identification of enzymes or proteins involved in conversion of tryptophan to the neuroactive compound 'i', wherein the identification of enzymes or proteins employ protein sequence or functional domain similarity search algorithms, wherein a filtration step is included based on presence of genes or functional domains of a particular pathway in proximity to each other in a genome of a particular organism to increase prediction efficiency, α—confidence value of the corresponding bacterial group, where the confidence value is evaluated based on the relative number of strains belonging to a particular genus, and β—'weightage' which represents an enrichment value of a particular pathway in a particular body site;

calculating, via the one or more hardware processors, a metabolic potential (MP) corresponding to each compound of the set of neuroactive compounds using the bacteria function matrix and the scaled bacterial abundance values, wherein the metabolic potential (MP) is indicative of the capability of the bacterial community for producing the neuroactive compound, wherein the metabolic potential (MP) is calculated using formula:

$$MP_{NAC} = \sum_{i=1}^{n} RA_i \times SCORBPEO_{[NAC][i]}$$

where, $MP_{NAC}$—Metabolic potential of the bacterial community (of interest) for production of a particular neuroactive compound, n—number of the particular neuroactive compound producing bacterial genera present in the bacterial community of interest, RA—relative scaled abundance of a particular bacterial genus 'i' predicted to have the metabolic pathway for the neuroactive compound production, and $SCORBPEO_{[NAC][i]}$—The 'SCORBPEO (Score for Bacterial Production of Neuro-active Compound)' score of genus 'i' for production of the particular neuroactive compound 'NAC';

generating, via the one or more hardware processors, a classification model utilizing the metabolic potential (MP) of each compound of the set of neuroactive compounds using machine learning techniques, wherein MP values corresponding to the set of neuro-active compounds are considered as features for training the classification model, wherein a sample set is randomly divided into training set samples and testing set samples;

predicting, via the one or more hardware processors, the risk of the person to develop or suffering from ASD is a significant risk, a low risk or no risk, using the classification model based on a predefined set of conditions, wherein the person has the significant or low risk;

designing therapeutic approaches, through targeting the bacterial groups that are capable of producing a set of neurotoxic compounds or facilitating growth of healthy microbes, wherein the set of neurotoxic compounds are compounds which negatively affect the functioning of the gut-brain axis, wherein designing the therapeutic approaches includes identification of a consortium of microbes to be used in the form of prebiotic or probiotic or symbiotic to (i) reduce growth of bacteria in the gut which are capable of producing the set of neurotoxic compounds and (ii) enhance the growth of beneficial bacteria in the gut which is capable of maintaining a healthy gut or produce the set neuroactive compounds which are beneficial for functioning and regulation of the gut-brain axis, wherein the identification of the consortium of microbes is performed based on the MP values of a bacterial genera identified in the sample, differentially abundant bacterial taxa in cohorts of autism patients and healthy persons and the SCORBPEO score values of the differentially abundant bacterial taxa corresponding to the production of the set of neuroactive compounds; and administering, to the person with the significant or low risk, the designed consortium of microbes for improved treatment of ASD, including minimization of side effects of therapeutic drugs through maintaining a healthy cohort of the bacteria in the gut, wherein the method is implemented for diagnosis or treatment of ASD.

2. The method according to claim 1, wherein the pre-defined set of conditions comprises comparing the metabolic potential for production of one of the set of neuroactive compounds with a threshold value, wherein the result of comparison is:

no risk of ASD if the metabolic potential is less than the threshold value, the low risk if the metabolic potential is between the threshold value and a third quartile value of a data set containing the metabolic potential values of the neuroactive compound, and the significant risk if the metabolic potential is more than the third quartile value of a data set containing the metabolic potential values of the neuroactive compound.

3. The method according to claim 1, wherein isolating and sequencing stretches of DNA further comprises at least one of:

amplifying and sequencing bacterial 16S rRNA, 23S rRNA, rpoB, cpn60 marker genes from the bacterial DNA, amplifying and sequencing one or more of a full-length or one or more specific regions of the bacterial 16S rRNA, 23S rRNA, rpoB, cpn60 marker genes from the microbial DNA, amplifying and sequencing one or more phylogenetic marker genes from the bacterial DNA, or whole genome shotgun sequencing (WGS) data corresponding to bacterial DNA, isolated from the body site of a person.

4. The method according to claim 1, wherein the sequencing is performed via one or more of: an amplicon sequencing, a whole genome shotgun sequencing (WGS), a fragment library based sequencing technique, a mate-pair library or a paired-end library based sequencing technique, a polymerase chain reaction (PCR), an RNA sequencing technique, or a microarray-based technique.

5. The method according to claim 1, wherein the step of pre-processing the microbial abundance data comprises nor-malizing to represent the abundance in form of scaled values, wherein the normalization on microbial counts is performed through one or more of a rarefaction, a quantile scaling, a percentile scaling, a cumulative sum scaling, or an Aitchison's log-ratio transformation.

6. The method according to claim 1, wherein the set of neuroactive compounds comprises one or more of Kynurenine, Quinolinate, Indole, Indole acetic acid (IAA), Indole propionic acid (IPA), and Tryptamine.

7. The method according to claim 1, wherein generating the classification model using machine learning techniques is performed using one or more of random forest, decision trees techniques, linear regression, logistic regression, naive Bayes, linear discriminant analyses, k-nearest neighbor algorithm, Support Vector Machines, and Neural Networks techniques.

8. The method according to claim 1, wherein the sample is one of saliva, stool, blood, body fluid, tissue, or swab.

9. The method according to claim 1, wherein the body site is one of a gut, oral, skin, or urinogenital tract of the person.

10. The method according to claim 1, wherein the healthy microbes include microbes producing neuro-protective compounds which have beneficial effects on the gut-brain axis.

11. The method according to claim 1, wherein values of the computed score is rescaled to 0-10, wherein for the particular pathway, a bacterial taxa having a higher SCORBPEO indicate a greater capability of production of a particular neuroactive compound as compared to a taxa with a lower SCORBPEO, wherein scaling of the bacterial abundance values is performed through one or more of: a percentage, a cumulative sum scaling, a minmax scaling, a maxAbs scaling, a robust scaling, a percentile, a quantile, or an Atkinson's log transformation, wherein sensitivity and specificity of the classification model are used for selecting a plurality of parameters to classify diseased samples from healthy samples.

12. The method according to claim 1, wherein the consortium of microbes is composed of Kynurenine to classify healthy samples and diseased samples, wherein the bacterial strains belonging to genera *Eubacterium* and *Clostridium* XIVa are administered as probiotic formulation in order to alleviate symptoms of ASD through maintaining a healthier gut microbiome, thereby improving an efficiency of current therapeutic approaches or minimizing the side effects of conventional therapies of ASD.

\* \* \* \* \*